US009260487B2

(12) United States Patent
Desai et al.

(10) Patent No.: US 9,260,487 B2
(45) Date of Patent: Feb. 16, 2016

(54) AXMI-205 PESTICIDAL GENE AND METHOD FOR ITS USE

(71) Applicant: Athenix Corp., Morrisville, NC (US)

(72) Inventors: Nalini Manoj Desai, Chapel Hill, NC (US); Jill Hinson, Rougemont, NC (US); Deepa Balasubramanian, Chapel Hill, NC (US); Kimberly S. Sampson, Durham, NC (US); Daniel J. Tomso, Bahama, NC (US); Duane Alan Lehtinen, Cary, NC (US); Nicholas B. Duck, Apex, NC (US); Rong Guo, Cary, NC (US); Volker Heinrichs, Wedemark (DE)

(73) Assignee: Athenix Corp., Morrisville, NC (US)

(*) Notice: Subject to any disclaimer, the term of this patent is extended or adjusted under 35 U.S.C. 154(b) by 195 days.

(21) Appl. No.: 14/057,250

(22) Filed: Oct. 18, 2013

(65) Prior Publication Data
US 2014/0051837 A1   Feb. 20, 2014

Related U.S. Application Data

(62) Division of application No. 12/828,594, filed on Jul. 1, 2010, now Pat. No. 8,575,425.

(60) Provisional application No. 61/222,778, filed on Jul. 2, 2009.

(51) Int. Cl.
| *C07K 16/00* | (2006.01) |
| *C07K 14/195* | (2006.01) |
| *C12Q 1/68* | (2006.01) |
| *C12N 15/82* | (2006.01) |
| *C07K 14/22* | (2006.01) |
| *C07K 16/12* | (2006.01) |

(52) U.S. Cl.
CPC ............... *C07K 14/195* (2013.01); *C07K 14/22* (2013.01); *C07K 16/1203* (2013.01); *C12N 15/8285* (2013.01); *C12N 15/8286* (2013.01); *C12Q 1/6876* (2013.01)

(58) Field of Classification Search
None
See application file for complete search history.

(56) References Cited

U.S. PATENT DOCUMENTS 7,692,068 B2   4/2010  Carozzi et al.

FOREIGN PATENT DOCUMENTS

| WO | 01/16305 | 3/2001 |
| WO | 2007/147096 | 12/2007 |
| WO | 2009/052242 | 4/2009 |
| WO | 2010/091230 | 8/2010 |
| WO | 2010/099365 | 9/2010 |
| WO | 2010/141141 | 12/2010 |
| WO | 2011/002992 | 1/2011 |

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Rosado, C.J. et al., Chain A, Structure of a MACPF Perforin-Like Protein, 2QP2 A., Science 317 (1548-1551 (2007), GenPept Accession No. 2QPZ-A, submitted Sep. 24, 2008.
Bowen, D. et al., Insecticidal Toxins From the Bacterium Photorhabdus Luminescens, Science, vol. 280, Jun. 26, 1998.
Cambell, C. et al., "Novel Insecticidal Proteins," 2006 Entomological Society of America Annual Meeting (poster D0234) Dec. 10-13, 2006, Indianapolis, Indiana.
Cambell, C. et al., "Novel Insecticidal Proteins," 2007 Entomological Society of America Annual Meeting (poster D0267), Dec. 9-12, 2007, San Diego, California.
De Maagd, Ruud, et al., How Bacillus Thuringiensis Has Evolved Specific Toxins to Colonize the Insect World, Trends in Genetics vol. 17, No. 4, Apr. 2001.
Iddo Friedberg, Automated Protein Function Prediction—The Genomic Challenge, Briefings in Bioinformatics, vol. 7, No. 3, 225-242.
Gartemann, Karl-Heinz, et al., The Genome Sequence of the Tomato-Pathogenic Actinomycete *Clavibacter michiganensis* subsp. *michiganensis* NCPPB382 Reveals a Large Island Involved in Pathogenicity, Journal of Bacteriology, Mar. 2008, p. 2138-2149, vol. 190, No. 6.
Grkovic, Steve, et al., Genes Essential for Amber Disease in Grass Grubs Are Located on the Large Plasmid Found in Serratia Entomophila and Serratis Proteamaculans, Applied and Environmental Microbiology, Jun. 1995, p. 2218-2223, vol. 61, No. 6, XP-000994571.

(Continued)

*Primary Examiner* — Jennifer Graser

(57) ABSTRACT

Compositions and methods for conferring pesticidal activity to bacteria, plants, plant cells, tissues and seeds are provided. Compositions comprising a coding sequence for pesticidal polypeptides are provided. The coding sequences can be used in DNA constructs or expression cassettes for transformation and expression in plants and bacteria. Compositions also comprise transformed bacteria, plants, plant cells, tissues, and seeds. In particular, isolated pesticidal nucleic acid molecules are provided. Additionally, amino acid sequences corresponding to the polynucleotides are encompassed. In particular, the present invention provides for nucleic acid molecules comprising nucleotide sequences encoding the amino acid sequence shown in SEQ ID NO:2, 3, or 4, the nucleotide sequence set forth in SEQ ID NO:1, 9, 10, or 11, as well as variants and fragments thereof.

1 Claim, 1 Drawing Sheet

(56) References Cited

OTHER PUBLICATIONS

Hurst, Mark, et al., Plasmid-Located Pathogenicity Determinants of Serratia Entomophila, The Causal Agent of Amber Disease of Grass Grub, Show Similarity to the Insecticidal Toxins of Photorhabdus Luminescens, Journal of Bacteriology, Sep. 2000, p. 5127-5138, vol. 182, No. 18, XP-002166799.

Jackson, Trevor A., et al., Pathogen to Product—Development of Serratia Entomophila (Enterobacteriaceae) as a Commercial Biological Control Agent for the New Zealand Grass Grub (Costelytra Zealandica), 1992, p. 191-198, XP-000997900.

Rosado, Carlos, et al., A Common Fold Mediates Vertebrate Defense and Bacterial Attack, Sep. 14, 2007, vol. 317 Science.

Rosado, Carlos, et al., The MACPF/CDC Family of Pore-Forming Toxins, Cellular Microbiology (2008), 10(9), 1765-1774.

Thissen Julia, et al., "Proteins for the Control of Plant-Parasitic Nematodes," 2007 American Phytopathological Society Annual Meeting (poster SP-173) Jul. 28-Aug. 1, 2007, San Diego, California.

S. Tounsi, et al., Cloning and Study of the Expression of a Novel CRY1LA-Type Gene From *Bacillus thuringiensis* subsp. *kurstaki*, Journal of Applied Microbiology 2003, 95, 23-28.

K. H. Gartemann, et al., Putative Perforin [*Clavibacter michiganensis* subsp. *michiganens*, J. Bacteriol. 190 (6), 2138-2149, (2008).

International Search Report for PCT/US2012/048496 mailed Jun. 11, 2012.

\* cited by examiner

```
                         *         20         *         40         *         60         *         80
Axmi205      : ------------------------MASAANAGQLGHLPGVTSHGHGYDVHGLYASPKSLLGQPLFHFGGELDSI------ :  50
Clavibacter  : ------------------------MSDFFVTETDTPPILPGVSLTGSTYDVFGDDATNDSAIFQIFDHSKAESGTT----- :  52
Photorhabdus : MSNDRTGKSLEQENSERDVEIPDRNYFRKLSLFDDTVIAGAEHIGTSYDVFGRYCNVGSCHNSLFDEPKINASEDNFKKV :  80
                                        f         6pGv   G  YDVfG ya    S 6 fd   k e

*        100         *        120         *        140         *        160
Axmi205      : EIEGRSYTFPRSMHVHTYFHSDFKQDVSKEIEEYREKMSQHVGVSGRYKLFSASLSVDFTTTDQQLTEITYSSTREAHVL : 130
Clavibacter  : EINGTEYRIPKLHNAEGVASSEYVSIYGNTVEEYQQSLAASVAVSGSNMFFSGSLETQFGSSSMPRSENAFSRVEQVVEL : 132
Photorhabdus : TILGETLKVPYYIDCYSVGBLEYINASGESIESYQSRISSKSRIKGNYLFFSASLKVDFDTDSLTDFENAFSRIQVTYDL : 160
                eI G  y  P  d     v  s S       g   6KeYq  6s  v  dsG  y fFSaSL vdF S  s    EnaSSr      L

*        180         *        200         *        220         *        240
Axmi205      : VYISLPGAATLPSELRRDFRDDLN---------NPNKPAHELFKRYGFYYISEAAVGGPLDYSAASKTLKMDSSQSLSTT : 201
Clavibacter  : VSIGLPPSKELRELLSGSFLKALPGLPAAASTSEEQAKYEGFLDTRGAFYLSGHLIGGKTLFTSSVNKLTVDRTLSISVT : 212
Photorhabdus : YILKSS--AEALKEFLEESVKTALD--------KADTEEDHNDLFNTWGSHFLSGVVHGGCAQYSSSTNKYTSNLTNSFDVV : 232
                     S     ip a   t4a L      sf    aLl              lf  tSG   56Sg   6GG      5Sas  nklt  l  S  avt

*        260         *        280         *        300         *        320
Axmi205      : AEHSYKALVGEIKIEHGSEHEKQVNSFRSNSTIRLTATGGKPG-----------MTDRILHGPDSQQAFSQWAESLLDYA : 270
Clavibacter  : ADLSYKSVTHQISNEDKIKYASQLSQFASSSNTVKNAFGSNP------------ALASRVFDGRVQYDEWSASVAQNF   : 278
Photorhabdus : AAASFAGFIG-LSARTGNSFHEDIKEFPSASNIKTHAIGGDLSPFDFGGATSAPQPSAEEIAAAKKAFEDWEASVPNAP  : 311
                A  SSk     G  6s  e  g         q6    FrS Sai    A  GG p                    a         d     aS  W aS6       p

*        340         *        360         *        380         *        400
Axmi205      : TLMDFS-TESLQPINALADHPERRVELEDAFPEFHPQSQQSIPKVPKVLLHDARPPHVKAGEPSGSGASEDLAVFNPSTS : 349
Clavibacter  : VIVRFDGTRPLTGVNTLCSTPEPGKILESYFDDKWAF-------------------APSLELSHFPDVVD           : 329
Photorhabdus : ELVNFADSNPLTGINELCSDRTQKAELKKHFETVWAF-------------------AESAERRVHADYID           : 362
                     6S  F    S  pLtg6N  Lcs  per        Le   F        waF                                    aS  l vf d   d

*        420         *        440         *        460         *        480
Axmi205      : NGYENVGQFGQRNHASVAPGHAPIFKDLFDLGVLKAPVGWGQRVHDDAGSGNSK---DYACHRAIPPQGYRALGDVMMLATS : 427
Clavibacter  : PLTVVVGNDDQF---------------------------PVPDGYTKDDYDLNSPHAGGKFIYLCNHKVPVSGLRKFKRVLQAMQV : 387
Photorhabdus : KIIIGINNTNTP---------------------------PEGYICLKSTKDENLNSFG-NICLFHHKAEYDPNIDNKDCITELKF : 419
                     6gn     qp                                              p    p g  4        D n         g     iylcvhk   p   q r   kdv6

*        500         *        520         *        540         *        560
Axmi205      : GYNPPNLPPYVCVHQSLCADVQTLQNFVWDKGTGARKDVSLHQPGAAGAVASSCFAGVPNYNWPPNSGDIERLPGSTAC : 507
Clavibacter  : IYNGPKVPDGYSKINVDLNQGAGGDDVFLCHKQGEYGTDENILDVPVIGG-NDSFVPAFYGYKTLPG-----DLNKGAGGD : 462
Photorhabdus : ITVPPESPEGOWVKIPQHIYISPNQYLYLCYLPAEYSAEKAIKDIQLLCSSCGSSKILPYGYNPVLDERGERANATEDDN : 499
                iyn dk Pdg   v             q    lc k  y  d  e  d           g       S       pygYn  p         n  g

*        580
Axmi205      : VKTSAIASMQEHRSHLSQHQGHEAHHSEL : 536
Clavibacter  : YVYIAYAN--------------------- : 470
Photorhabdus : VHYLIYSAGHK------------------ : 510
                v  y  aya
```

AXMI-205 PESTICIDAL GENE AND METHOD FOR ITS USE

CROSS REFERENCE TO RELATED APPLICATIONS

This application is a divisional of U.S. patent application Ser. No. 12/828,594, filed Jul. 1, 2010, which claims the benefit of U.S. Provisional Application Ser. No. 61/222,778, filed Jul. 2, 2009, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "APA066US01DSeqList," created on Oct. 12, 2013, and having a size of 63 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

Introduction of DDT (dichloro-diphenyl-trichloroethane) and the following move towards indiscriminate use of synthetic chemical insecticides led to the contamination of water and food sources, poisoning of non-target beneficial insects and development of insect pests resistant to the chemical insecticides. Increased public concerns about the adverse environmental effects of indiscriminate use of chemical insecticides prompted a search for alternative methods for insect pest control.

One of the promising alternatives has been the use of biological control agents. There is well-documented history of safe application of Bt (*B. thuringiensis*, a gram positive soil bacterium) as effective biopesticides and a number of reports of expression of delta-endotoxin gene(s) in crop plants are available. Only a few insecticidal sprays are required on Bt transgenic crops, which not only save cost and time, but also reduce health risks. In some cases, insects can develop resistance to different insecticidal compounds, which raises the need to identify alternative biological control agents for pest control.

SUMMARY OF INVENTION

Compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated or recombinant nucleic acid molecules are provided that encode a pesticidal protein. Additionally, amino acid sequences corresponding to the pesticidal protein are encompassed. In particular, the present invention provides for an isolated nucleic acid molecule comprising a nucleotide sequence encoding the amino acid sequence shown in SEQ ID NO:2, 3, 4, 5, 6, 7, or 8 or a nucleotide sequence set forth in SEQ ID NO:1, 9, 10, or 11, as well as variants and fragments thereof. Nucleotide sequences that are complementary to a nucleotide sequence of the invention, or that hybridize to a sequence of the invention are also encompassed.

Methods are provided for producing the polypeptides of the invention, and for using those polypeptides for controlling or killing a lepidopteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

BRIEF DESCRIPTION OF THE FIGURES

FIG. 1 shows an alignment of AXMI-205 (SEQ ID NO:2) with MACPF proteins from *Photorhabdus luminescens* (SEQ ID NO:14) and *Clavibacter michiganensis* (SEQ ID NO:15).

DETAILED DESCRIPTION

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of bacterial species. The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling. The proteins find use in controlling or killing lepidopteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the Lepidoptera, Diptera, and Coleoptera orders, or the Nematoda phylum, or a protein that has homology to such a protein. Pesticidal proteins have been isolated from organisms including, for example, *Bacil-*

*lus* sp., *Clostridium bifermentans* and *Paenibacillus popilliae*. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Thus, provided herein are novel isolated or recombinant nucleotide sequences that confer pesticidal activity. Also provided are the amino acid sequences of the pesticidal proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid sequence (or DNA) is used herein to refer to a nucleic acid sequence (or DNA) that is no longer in its natural environment, for example in an in vitro or in a recombinant bacterial or plant host cell. In some embodiments, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated nucleic acid molecule encoding a pesticidal protein can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A pesticidal protein that is substantially free of cellular material includes preparations of protein having less than about 30%, 20%, 10%, or 5% (by dry weight) of non-pesticidal protein (also referred to herein as a "contaminating protein").

Nucleotide sequences encoding the proteins of the present invention include the sequence set forth in SEQ ID NO:1, 9, 10, or 11, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the pesticidal protein encoded by this nucleotide sequence are set forth in SEQ ID NO:2, 3, or 4.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400, 1450, 1500, 1550, 1600 contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. By "retains activity" is intended that the fragment will have at least about 30%, at least about 50%, at least about 70%, 80%, 90%, 95% or higher of the pesticidal activity of the pesticidal protein. In one embodiment, the pesticidal activity is coleoptericidal activity. In another embodiment, the pesticidal activity is lepidoptericidal activity. In another embodiment, the pesticidal activity is nematocidal activity. In another embodiment, the pesticidal activity is diptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450, 500, 550, or 600 contiguous amino acids, or up to the total number of amino acids present in a full-length pesticidal protein of the invention. In some embodiments, the fragment is an N-terminal or a C-terminal truncation of at least about 1, 2, 3, 4, 5, 6, 7, 8, 9, 10, 11, 12, 13, 14, 15, 16, 17, 18, 19, 20, 25 or more amino acids relative to SEQ ID NO:2, 3, or 4. In some embodiments, the fragments encompassed herein result from the removal of the C-terminal 1, 2, 3, 4, 5, 6, 7, 8, 9, 10, 11, 12, 13, 14, 15, 16, 17, 18, 19, 20, 25 or more amino acids, e.g., by proteolysis or by insertion of a stop codon in the coding sequence.

Preferred pesticidal proteins of the present invention are encoded by a nucleotide sequence sufficiently identical to the nucleotide sequence of SEQ ID NO:1, 9, 10, or 11. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the comparison is across the entirety of the reference sequence (e.g., across the entirety of one of SEQ ID NO:1, 9, 10, or 11, or across the entirety of one of SEQ ID NO:2, 3, 4, 5, 6, 7, or 8). The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A nonlimiting example of a software program useful for analysis of ClustalW alignments is GENEDOC™. GENEDOC™ (Karl Nicholas) allows assessment of amino acid (or DNA) similarity and identity between multiple proteins. Another nonlimiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10. The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, retaining pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal protein sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Pesticidal proteins are also encompassed within the present invention. By "pesticidal protein" is intended a protein having the amino acid sequence set forth in SEQ ID NO:2, 3, or 4. Fragments, biologically active portions, and variants thereof (e.g., SEQ ID NO:5, 6, 7, and 8) are also provided, and may be used to practice the methods of the present invention. An "isolated protein" is used to refer to a protein that is no longer in its natural environment, for example in vitro or in a recombinant bacterial or plant host cell.

"Fragments" or "biologically active portions" include polypeptide fragments comprising amino acid sequences sufficiently identical to the amino acid sequence set forth in SEQ ID NO:2, 3, or 4, and that exhibit pesticidal activity. A biologically active portion of a pesticidal protein can be a polypeptide that is, for example, 10, 25, 50, 100, 150, 200, 250 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:2, 3, or 4. The invention encompasses other fragments, however, such as any fragment in the protein greater than about 10, 20, 30, 50, 100, 150, 200, 250, 300, 350, 400, 450, 500, 550 or more amino acids.

In some embodiments, the fragment is an N-terminal or a C-terminal truncation of at least about 1, 2, 3, 4, 5, 6, 7, 8, 9, 10, 11, 12, 13, 14, 15, 16, 17, 18, 19, 20, 25 or more amino acids relative to SEQ ID NO:2, 3, or 4 (e.g., SEQ ID NO:7 or 8). In some embodiments, the fragments encompassed herein result from the removal of the C-terminal 1, 2, 3, 4, 5, 6, 7, 8, 9, 10, 11, 12, 13, 14, 15, 16, 17, 18, 19, 20, 25 or more amino acids, e.g., by proteolysis or by insertion of a stop codon in the coding sequence.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of SEQ ID NO:2, 3, 4, 5, 6, 7, or 8. Variants also include polypeptides encoded by a nucleic acid molecule that hybridizes to the nucleic acid molecule of SEQ ID NO:1, 9, 10, or 11, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

In some embodiments, the variant protein or polypeptide comprises one or more substitutions at the amino acid positions selected from the group consisting of positions 307, 315, 317, 349, 351, 353, 355, 395, 399, 407, 419, 435, 443, 465, 467, 483, 487, 495, 497, 499, 509, and 513 relative to SEQ ID NO:2. In specific embodiments, the substitution is an alanine for the native amino acid at the recited position(s). Also encompassed are the nucleotide sequence(s) encoding the variant protein or polypeptide.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. For example, SEQ ID NO:3 and 4 represent alternate start site proteins encoded by SEQ ID NO:1. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present invention and may be used in the methods of the present invention. It will be understood that, when expressed in plants, it will be necessary to alter the alternate start codon to ATG for proper translation.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of SEQ ID NO:2, 3, or 4, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the pesticidal protein mutations in a non-mutagenic strain, and identify mutated genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265: 20923-20930; Rang et al. 91999) *Appl. Environ. Microbiol.* 65:2918-2925).

Vectors

A pesticidal sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the pesticidal sequences disclosed herein. In various embodiments, the transgenic plant further comprises one or more additional genes for insect resistance, for example, one or more additional genes for controlling coleopteran, lepidopteran, heteropteran, or nematode pests. It will be understood by one of skill in the art that the transgenic plant may comprise any gene imparting an agronomic trait of interest.

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, *Macadamia*, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Use in Pesticidal Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

Pesticidal Compositions

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenization, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, dipteran, heteropteran, nematode, or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethon-methyl, Pirimicarb, Methiocarb; Maize Herbicides: Atrazine, Alachlor, Bromoxynil, Acetochlor, Dicamba, Clopyralid, (S-) Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin, Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino] furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobacsodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino] furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2 (5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran, Organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino] furan-2(5H)-on.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis* barberi, northern corn rootworm; *Diabrotica undecimpunctata* howardi, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus* leucopterus, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus* leucopterus, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest.

As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing a pesticidal protein disclosed herein. Expression of the pesticidal protein results in a reduced ability of a pest to infest or feed on the plant, thus improving plant yield.

The following examples are offered by way of illustration and not by way of limitation.

EXPERIMENTAL

Example 1

Identification of a Protein Active Against Western Corn Rootworm from Strain ATX 2024

The Western Corn Rootworm active protein AXMI-205 was identified by a combination of biochemistry and genomics analysis from Strain ATX 2024.

ATX2024 was identified as an active strain in *Diabrotica virgifera* (Western Corn Rootworm or WCRW) bioassay exhibiting a heat sensitive activity. Protein fractionation and purification were performed on ATX2024 culture materials as follows:

Cells of ATX2024 were grown in a suitable media (such as C2 media or CYS media supplemented with trehalose; the choice of media not being critical to the invention) for 3 days at 37° C. The incubation can also be performed at 30° C. Cell pellets were collected and cells disrupted in Buffer A (20 mM sodium acetate/50 mM sodium chloride, pH 5) using a "French Press" high pressure cell.

Lysates were clarified by centrifugation and dialyzed against 20 mM sodium acetate, 50 mM sodium chloride, pH 5.0. The dialyzed sample was then loaded onto a 20 ml SP Sepharose™ cation exchange column (GE Healthcare). Proteins were eluted with a linear salt gradient in Buffer A from 50 mM to 1M sodium chloride over 20 column volumes. The elution can also be performed over 10 column volumes.

Active fractions were pooled and dialyzed against Buffer B (20 mM Tris-HCl/50 mM NaCl, pH 7 or pH 8). Dialyzed active fractions were then loaded on a 5 ml sepharose Q anion exchange column. Other anion exchange columns can be used, e.g., the 1.7 ml SOURCE™Q anion exchange column. Proteins were eluted with a linear salt gradient in Buffer A from 50 mM to 1M NaCl. Collected fractions tested for activity on WCRW and fractions with activity on WCRW were observed. A protein band of approximately 52 kDa was identified as correlating with activity of fractions. This protein is referred to herein as Protein Band #10.

Active fractions were then pooled and concentrated, and subjected to SDS-PAGE. The portion of the resulting gel corresponding to protein band #10 was isolated, and was submitted for analysis by both N-terminal sequencing and matrix-assisted laser desorption ionization tandem time-of-flight mass spectrometry (MALDI-TOF-TOF) analyses as known in the art.

Comparison of MALDI-TOF-TOF data from Protein Band #10 showed no matches to a database of known proteins.

Amino acid sequencing of the N terminus of Protein Band #10 resulted in an N-terminal peptide sequence that showed no matches to known protein sequences when compared to a database of known protein sequences.

Example 2

Genomic Sequencing of ATX2024

The complete gene sequence was identified from the selected strain as follows:

Total DNA contains a mixture of some or all of the following: genomic DNA, plasmids of various size; phage chromosomes; other uncharacterized extrachromosomal molecules.

Mechanical or enzymatic shearing of the extrachromosomal DNA to generate size-distributed fragments.

Sequencing of the fragmented DNA by methods known in the art.

Example 3

Matching of N-terminal and MALDI-TOF-TOF Data to Genomic Sequence Data

A set of putative open reading frames (ORFs) encoded by the sequence data for ATX2024 was generated by extracting all possible ORFs from the sequence reads generated from ATX2024. N-terminal sequencing data from protein band #10 (above) were compared to the set of ATX2024 ORFs using the BLAST algorithm. Two reads were found to encode putative protein fragments with high homology to the N-terminal sequence data.

Similarly, MALDI-TOF-TOF data from protein band #10 were compared to the set of ATX2024 ORFs using the Mascot program (www.matrixscience.com; Perkins et al. (1999) *Electrophoresis* 20(18):3551-67). Seven reads were found to encode putative protein fragments having significant matches to peaks present in the MALDI-TOF-TOF data set.

The DNA sequence reads identified from N-terminal and MALDI-TOF-TOF data analysis were assembled to provide a preliminary gene sequence.

TAIL-PCR strategies were used to obtain flanking sequence adjacent to the preliminary gene sequence data. The sequences of the resulting PCR products were co-assembled with the original genomic data from ATX2024 to provide a finished gene sequence for the open reading frame encoding Protein Band #10. This open reading frame is designated as Axmi205 (SEQ ID NO:1), and the protein encoded by the open reading frame as AXMI-205 (SEQ ID NO:2, 3, or 4).

The genomic region encoding AXMI-205 was then amplified from the ATX2024 genome, cloned, and the DNA sequence of this clone obtained. The DNA sequence of this clone in the region encompassing Axmi205 is provided as SEQ ID NO:12.

Comparison of AXMI-205 with known protein sequence databases shows that AXMI-205 is a unique protein, showing very low homology (20% or less) to known proteins.

Interestingly, AXMI-205 does show low, but possibly significant, homology to a broad class of loosely related proteins often referred to as MACPF proteins (Rosado et al, Cellular Microbiology (2008) 10(9), 1765-1774). These proteins have been proposed to have roles in processes such as immune response and protection from bacterial attack. AXMI-205 is 20% identical to a protein from *Clavibacter michiganensis* (SEQ ID NO:14; GENBANK Accession No. YP_001223127, Gartemann et al, J. Bacteriol. 190 (6), 2138-2149 (2008)) and 13% identity to a *Photorhabdus luminescens* protein (SEQ ID NO:15; GENBANK Accession No. 2QP2_A; Rosado, C. J., et al, Science 317 (5844), 1548-1551 (2007)). Although these percent identities are low, one can identify blocks of amino acid conservation between these proteins from inspection of FIG. 1.

Example 3

Heterologous Expression of AXMI-205

The open reading frame of Axmi205 was cloned into an *E. coli* expression vector based on (1) maltose binding fusion vector to yield pAX6911, and (2) an expression vector based on pRSF1b to yield pAX7011.

For expression in *E. coli*, BL21*DE3 was transformed with either pAX6911, pAX7011, or control plasmids. A single colony transformed with the vector was inoculated in LB supplemented with kanamycin and grown overnight at 37° C. The following day, fresh medium was inoculated in duplicate with 1% of overnight culture and grown at 37° C. to logarithmic phase. Subsequently, cultures were induced with 1 mM IPTG for 3 hours at 37° C. or overnight at 20° C. Each cell pellet was suspended in 50 mM sodium carbonate buffer, pH 10.5 supplemented with 1 mM DTT and sonicated. Analysis by SDS-PAGE detected expression of a protein corresponding to the predicted size of AXMI-205. In the case of the pMal fusion vector pAX6911, a protein consistent with the predicted size for the pMAL-AXMI-205 fusion was observed by PAGE.

Example 4

Pesticidal Activity of AXMI-205

Fusion protein was purified from lysates of *E. coli* clones as recommended by the supplier (New England Biolabs), and cleaved with either Factor $X_a$ or trypsin. Cleavage of the purified fusion protein was confirmed by SDS-PAGE analysis. Purified protein from pAX6911 containing AXMI-205 and either pAX6911 cleaved with Factor Xa or Tryp sin, or uncleaved protein were tested in insect assays with appropriate controls in a buffer composed of 20 mM Tris, 1 mM DTT, 50 mM NaCl. Soluble extracts of pAX7011 expressing AXMI-205 were also tested in this manner. After two days, samples containing AXMI-205 exhibited strong stunting activity and conferred mortality on Western Corn Rootworm.

Table 1 shows a description of the scoring assignments used herein, and Table 2 summarizes the activities observed from AXMI-205 samples.

TABLE 1

Description of Scoring System

| Score | Description |
|---|---|
| 0 | no effect observed |
| 1 | mild non-uniform stunting |
| 2 | moderate non-uniform stunting |
| 3 | moderate to severe uniform stunting |
| 4 | mortality (<100%) with uniform stunting |
| 5 | complete mortality |

TABLE 2

Pesticidal Activity of AXMI-205 samples.

| Sample | WCRW Activity (2 days) | Percent Mortality |
|---|---|---|
| Axmi205 MBP fusion (from pAX6911) | 3.0 | 25% |
| Axmi205 MBP fusion cleaved with Factor Xa | 3.0 | 25% |
| Axmi205 MBP fusion cleaved with trypsin | 3.0 | 25% |
| Axmi205 in soluble extract from pAX7011 | 3.0 | 0% |
| Buffer Control | 0 | 0% |

Example 5

Additional Assays for Pesticidal Activity

The nucleotide sequences of the invention can be tested for their ability to produce pesticidal proteins. The ability of a pesticidal protein to act as a pesticide upon a pest is often assessed in a number of ways. One way well known in the art is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests and Journal of Economic Entomology* or by discussion with members of the Entomological Society of America (ESA).

Example 6

Synthetic Genes

Synthetic genes encoding AXMI-205 were designed. Axmi205v01.02 is set forth in SEQ ID NO:9. Axmi205v01.03 is set forth in SEQ ID NO:10. Axmi205v01.04 is set forth in SEQ ID NO:11.

Example 7

Variants of AXMI-205

To identify regions and positions in the C-terminal portion of AXMI-205 that are functionally important, alanine scanning mutants were assayed in the region corresponding to amino acid positions 307-536 of SEQ ID NO:2. The alanine mutants were generated synthetically (Geneart, Burlingame, Calif.) and were organized in an expression vector derived from pAX3577 for expression in *E. coli* (pAX3577 contains Axmi250v01.03 in pRSF1b(Invitrogen)).

Starting with mutant S307A, every second residue was substituted with an alanine. The last alanine mutant in this series was K535A. In total, 101 alanine mutants were pooled.

The pooled alanine mutants, as well as pAX3577, were transformed into BL21*DE3 cells and plated on LB+Kanamycin (100 µg/ml). Fresh colonies were picked into 8 ml LB+Kanamycin (100 µg/ml) liquid medium and were grown in 24 deep well blocks at 37° C. and 300 rpm until an OD600 nm of 0.6 was reached. IPTG was added to a final concentration of 0.5 mM and the cultures were incubated for an additional 18 hours at 20° C. The OD600 nm was determined and the cells were collected by centrifugation (10 minutes at 4000 rpm, 4° C.). The cell pellets were resuspended in 20 mM Tris/HCl pH7.4, 150 mM NaCl, 1 mM DTT at a density of 20 OD600/ml. The cells were disrupted by bead beating and soluble extracts were obtained after centrifugation at 4500 rpm for 15 minutes at 4° C.

The extracts were assayed for activity against WCRW at four replicates per variant each. After five and six days, rootworm toxicity scores were determined by averaging the scores from the four replicates. 266 variants were screened in this primary screen, providing a 3-fold coverage of the library. Variants scoring above and below the score of the Axmi205 wild-type sequence were sequenced.

The following alanine mutants (relative to SEQ ID NO:2) were found to be active on WCRW: S307A, D315A, V317A, S349A, G351A, K353A, V355A, D395A, G399A, W407A, G419A, P355A, P435A, S443A, K465A, V467A, F483A, P487A, S495A, D497A, E499A, K509A, and I513A. The alanine mutant E499A was designated Axmi205(evo24) (SEQ ID NO:5) and the alanine mutant V467A was designated Axmi205(evo25) (SEQ ID NO:6).

Example 8

Activity of Truncations of Axmi-205

Several truncations of axmi-205 were constructed and tested for activity on western corn rootworm. C-terminal truncations were constructed that removed either 10, 20, 30, 34, or 71 amino acids from the C-terminus of the AXMI-205 protein (SEQ ID NO:2).

Clone pAX7106 expressed an MBP fusion that, after cleavage with factor Xa, produced the protein AXMI-205 (trunc10) (SEQ ID NO:7), which is lacking 10 amino acids from the C-terminus relative to AXMI-205. Clone pAX7106 expressed an MBP fusion protein that, after cleavage with factor Xa, produced the protein AXMI-205(trunc20) (SEQ ID NO:8), which is lacking 20 amino acids from the C-terminus relative to AXMI-205. Both AXMI-205(trunc10) and AXMI-205(trunc20) demonstrated activity on WCRW, whereas a truncation of 30 amino acids did not.

Example 9

Vectoring of Genes for Plant Expression

The coding regions of the invention are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

In one aspect of the invention, synthetic DNA sequences are designed and generated. These synthetic sequences have altered nucleotide sequence relative to the parent sequence, but encode proteins that are essentially identical to the parent AXMI-205 protein (e.g., SEQ ID NO:9-12).

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENBANK® ID GI:14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif, SEQ ID NO:13) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the amino acid sequence of the invention, as well as the KDEL sequence at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

Example 10

Vectoring Genes for Plant Expression

The coding region DNA of the genes of the invention are operably connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter—gene—terminator constructs also are well known in the art.

The plant expression cassettes described above are combined with an appropriate plant selectable marker to aid in the selections of transformed cells and tissues, and ligated into plant transformation vectors. These may include binary vectors from *Agrobacterium*-mediated transformation or simple plasmid vectors for aerosol or biolistic transformation.

Example 11

Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

DN62A5S Media

| Components | Per Liter | Source |
|---|---|---|
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 12

Transformation of Genes of the Invention in Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

Example 13

Protection of Transgenic Plants Expressing Axmi205 from Root Damage Upon Infestation with Western Corn Rootworm Transgenic maize plants transformed with either of two versions of Axmi205 (Axmi205 (SEQ ID NO:1) or Axmi205v01.03 (SEQ ID NO:10)) were obtained by *Agrobacterium*-mediated transformation. Plants shown by PCR analysis to contain the appropriate Axmi205 construct were selected, and transferred to root trainer containers.

To plants containing Axmi205 or Axmi205v01.03 were transplanted to root-trainer containers and propagated for approximately three weeks. Individual plants were then each infested with ~125 non-diapausing western corn rootworm (*Diabrotica virgifera*) eggs. Greater than 90% of the eggs were observed to have hatched within 24 hours of infestation. Plants were analyzed for expression of AXMI-205 protein by Western blot analysis using an anti-AXMI-205 antibody. Plants expressing detectable amounts of AXMI-205 were selected for analysis. After fifteen days, the amount of root damage in each plant was assessed using the Iowa State node injury scale 1 (Oleson, J. D., Y. Park, T. M. Nowatzki, and J. J. Tollefson. 2005. *J. Econ Entomol.* 98(1): 1-8). Table 3 shows that both forms of AXMI-205 resulted in lower root damage than control plants infested in the same manner. In similar experiments, plants containing either Axmi205v01.02 or Axmi-205v01.04 demonstrated improved root ratings compared to the nontransformed controls (not shown).

TABLE 3

Root damage from transgenic maize expressing Axmi-205

| Transgene | Number of Plants | Average Root Score | Variance |
|---|---|---|---|
| Control plants (no transgene) | 35 | 2.44 | 0.23 |
| Axmi205 | 16 | 1.11 | 0.5 |
| Axmi205v01.03 | 12 | 0.81 | 0.43 |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated antibody that selectively binds to a recombinant polypeptide with pesticidal activity, wherein said recombinant polypeptide is selected from the group consisting of a polypeptide consisting of the amino acid sequence of any of SEQ ID NO:2, 3, 4, 5, 6, 7, or 8.

* * * * *

SEQUENCE LISTING

<160> NUMBER OF SEQ ID NOS: 15

<210> SEQ ID NO 1
<211> LENGTH: 1608
<212> TYPE: DNA
<213> ORGANISM: Chromobacterium sp.

<400> SEQUENCE: 1

```
atggcatccg cagcaaatgc aggtcagctt ggcaacctcc ccggcgttac ttccatgggc      60
atgggctatg acgtgaatgg tttgtacgcc agcccggaaa gcctgcttgg ccaacccttg     120
```

```
ttcgatttcg gcggcgagct ggacagcatc gaaatcgagg gccgcagcta cacctttccc    180
cgcagcatgc atgtacacac ctatttccat tccgacttca acaggatgt cagcaaggaa     240
atcgaagagt atcgggagaa atgagccag cacgtgggcg tgtccggccg ctacaagttg     300
ttcagcgctt cgctgagcgt ggatttcacc accacggacc agcaactgac cgagattacc    360
tacagctcca cccgcgaagc ccatgtgctg tggtacatca gcctgcctgg cgcggccacg    420
ctgcgttcga tgctgcgccg cgatttccgc gacgacctga caacccccaa tatgccggcc    480
atggagctgt tcaagcgcta tggtccctac tacatatcgg aagcggcggt gggcggccgg    540
ctggactaca gcgcggccag caagaccttg aagatggaca gcagccagtc gctgtccacc    600
accgccgaaa tgtcctacaa ggcgctggtg ggcgagatca agatcgagca tggctcggag    660
atggaaaagc aggtcaacag cttccgcagc aactccacca tccgtctcac cgccaccggc    720
ggcaagccgg gcatgaccga tcgcatactg cacggtccgg attcgcagca ggcgttctcg    780
caatgggcgg aatcgctgct cgactatgcg acgctgatgg actttccac cgaaaagcctg    840
caaccgatct gggcgctggc cgacaagccc gagcgccgcg tcgagcttga ggacgccttc    900
cccgaattca tgaagcagtc gcagcagtcc atccccaagg tggacaaggt gctgctgatg    960
gacgcgcggc cgcctatggt gaaggctggg gaggatagcg gctccggcgc gtcggaggat   1020
ctggctgtgt tcaatcccag cacctccaat ggctacaaga tggttggcca gttcggtcag   1080
cgcaaccatg ccagcgtggc ggatggccat gcgccgattt caaggatct gttcgatctg    1140
ggcgtgctga aggcgccggt gggttggcag cgggtgtggg acgacgccgg ctccggcaag   1200
tccaaggact acgcgtgctg gcgcgcgatt ccgccgcagg gctaccgcgc gctgggcgat   1260
gtgatgatgc tggccaccag cggctataac ccgccgaatc tgccggacta tgtttgcgtg   1320
catcaaagcc tgtgcgcgga tgtgcagacg ctgcaaaacc gggtgtggtg ggacaagggc   1380
accggcgcgc gcaaggatgt cagcctgtgg caaccgggcg cggccggcgc ggtggcgtcc   1440
tcttgcttcg ccggcgtgcc taattacaac aacccgccca attccggcga catcgagcgc   1500
ttgcgcggca gcatcgcatg cgtgaagacc agcgcgatcg cgtccatgca ggaaatgaag   1560
tccatgctca gccagcacca aggcatggaa gcgatgatgt ccaagctg               1608
```

<210> SEQ ID NO 2
<211> LENGTH: 536
<212> TYPE: PRT
<213> ORGANISM: Chromobacterium sp.

<400> SEQUENCE: 2

```
Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110
```

```
Asp Gln Gln Leu Thr Glu Ile Thr Tyr Ser Ser Thr Arg Glu Ala His
            115                 120                 125

Val Leu Trp Tyr Ile Ser Leu Pro Gly Ala Ala Thr Leu Arg Ser Met
130                 135                 140

Leu Arg Arg Asp Phe Arg Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ser Lys Thr Leu Lys Met
                180                 185                 190

Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
            290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
            370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
            450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Asn Ser Gly
                485                 490                 495

Asp Ile Glu Arg Leu Arg Gly Ser Ile Ala Cys Val Lys Thr Ser Ala
                500                 505                 510

Ile Ala Ser Met Gln Glu Met Lys Ser Met Leu Ser Gln His Gln Gly
            515                 520                 525

Met Glu Ala Met Met Ser Lys Leu
```

<210> SEQ ID NO 3
<211> LENGTH: 518
<212> TYPE: PRT
<213> ORGANISM: Chromobacterium sp.

<400> SEQUENCE: 3

Met Gly Met Gly Tyr Asp Val Asn Gly Leu Tyr Ala Ser Pro Glu Ser
1               5                   10                  15

Leu Leu Gly Gln Pro Leu Phe Asp Phe Gly Gly Glu Leu Asp Ser Ile
            20                  25                  30

Glu Ile Glu Gly Arg Ser Tyr Thr Phe Pro Arg Ser Met His Val His
        35                  40                  45

Thr Tyr Phe His Ser Asp Phe Lys Gln Asp Val Ser Lys Glu Ile Glu
    50                  55                  60

Glu Tyr Arg Glu Lys Met Ser Gln His Val Gly Val Ser Gly Arg Tyr
65                  70                  75                  80

Lys Leu Phe Ser Ala Ser Leu Ser Val Asp Phe Thr Thr Thr Asp Gln
                85                  90                  95

Gln Leu Thr Glu Ile Thr Tyr Ser Thr Arg Glu Ala His Val Leu
            100                 105                 110

Trp Tyr Ile Ser Leu Pro Gly Ala Ala Thr Leu Arg Ser Met Leu Arg
        115                 120                 125

Arg Asp Phe Arg Asp Asp Leu Asn Asn Pro Asn Met Pro Ala Met Glu
130                 135                 140

Leu Phe Lys Arg Tyr Gly Pro Tyr Tyr Ile Ser Glu Ala Ala Val Gly
145                 150                 155                 160

Gly Arg Leu Asp Tyr Ser Ala Ala Ser Lys Thr Leu Lys Met Asp Ser
                165                 170                 175

Ser Gln Ser Leu Ser Thr Thr Ala Glu Met Ser Tyr Lys Ala Leu Val
            180                 185                 190

Gly Glu Ile Lys Ile Glu His Gly Ser Glu Met Glu Lys Gln Val Asn
        195                 200                 205

Ser Phe Arg Ser Asn Ser Thr Ile Arg Leu Thr Ala Thr Gly Gly Lys
210                 215                 220

Pro Gly Met Thr Asp Arg Ile Leu His Gly Pro Asp Ser Gln Gln Ala
225                 230                 235                 240

Phe Ser Gln Trp Ala Glu Ser Leu Leu Asp Tyr Ala Thr Leu Met Asp
                245                 250                 255

Phe Ser Thr Glu Ser Leu Gln Pro Ile Trp Ala Leu Ala Asp Lys Pro
            260                 265                 270

Glu Arg Arg Val Glu Leu Glu Asp Ala Phe Pro Glu Phe Met Lys Gln
        275                 280                 285

Ser Gln Gln Ser Ile Pro Lys Val Asp Lys Val Leu Leu Met Asp Ala
290                 295                 300

Arg Pro Pro Met Val Lys Ala Gly Glu Asp Ser Gly Ser Gly Ala Ser
305                 310                 315                 320

Glu Asp Leu Ala Val Phe Asn Pro Ser Thr Ser Asn Gly Tyr Lys Met
                325                 330                 335

Val Gly Gln Phe Gly Gln Arg Asn His Ala Ser Val Ala Asp Gly His
            340                 345                 350

Ala Pro Ile Phe Lys Asp Leu Phe Asp Leu Gly Val Leu Lys Ala Pro
        355                 360                 365

```
Val Gly Trp Gln Arg Val Trp Asp Asp Ala Gly Ser Gly Lys Ser Lys
    370                 375                 380

Asp Tyr Ala Cys Trp Arg Ala Ile Pro Pro Gln Gly Tyr Arg Ala Leu
385                 390                 395                 400

Gly Asp Val Met Met Leu Ala Thr Ser Gly Tyr Asn Pro Pro Asn Leu
                405                 410                 415

Pro Asp Tyr Val Cys Val His Gln Ser Leu Cys Ala Asp Val Gln Thr
                420                 425                 430

Leu Gln Asn Arg Val Trp Trp Asp Lys Gly Thr Gly Ala Arg Lys Asp
            435                 440                 445

Val Ser Leu Trp Gln Pro Gly Ala Gly Ala Val Ala Ser Ser Cys
450                 455                 460

Phe Ala Gly Val Pro Asn Tyr Asn Asn Pro Pro Asn Ser Gly Asp Ile
465                 470                 475                 480

Glu Arg Leu Arg Gly Ser Ile Ala Cys Val Lys Thr Ser Ala Ile Ala
                485                 490                 495

Ser Met Gln Glu Met Lys Ser Met Leu Ser Gln His Gly Met Glu
                500                 505                 510

Ala Met Met Ser Lys Leu
            515
```

```
<210> SEQ ID NO 4
<211> LENGTH: 516
<212> TYPE: PRT
<213> ORGANISM: Chromobacterium sp.

<400> SEQUENCE: 4

Met Gly Tyr Asp Val Asn Gly Leu Tyr Ala Ser Pro Glu Ser Leu Leu
1               5                   10                  15

Gly Gln Pro Leu Phe Asp Phe Gly Gly Glu Leu Asp Ser Ile Glu Ile
                20                  25                  30

Glu Gly Arg Ser Tyr Thr Phe Pro Arg Ser Met His Val His Thr Tyr
            35                  40                  45

Phe His Ser Asp Phe Lys Gln Asp Val Ser Lys Glu Ile Glu Glu Tyr
    50                  55                  60

Arg Glu Lys Met Ser Gln His Val Gly Val Ser Gly Arg Tyr Lys Leu
65                  70                  75                  80

Phe Ser Ala Ser Leu Ser Val Asp Phe Thr Thr Thr Asp Gln Gln Leu
                85                  90                  95

Thr Glu Ile Thr Tyr Ser Ser Thr Arg Glu Ala His Val Leu Trp Tyr
                100                 105                 110

Ile Ser Leu Pro Gly Ala Ala Thr Leu Arg Ser Met Leu Arg Arg Asp
            115                 120                 125

Phe Arg Asp Asp Leu Asn Asn Pro Asn Met Pro Ala Met Glu Leu Phe
    130                 135                 140

Lys Arg Tyr Gly Pro Tyr Tyr Ile Ser Glu Ala Ala Val Gly Gly Arg
145                 150                 155                 160

Leu Asp Tyr Ser Ala Ala Ser Lys Thr Leu Lys Met Asp Ser Ser Gln
                165                 170                 175

Ser Leu Ser Thr Thr Ala Glu Met Ser Tyr Lys Ala Leu Val Gly Glu
                180                 185                 190

Ile Lys Ile Glu His Gly Ser Glu Met Glu Lys Gln Val Asn Ser Phe
            195                 200                 205

Arg Ser Asn Ser Thr Ile Arg Leu Thr Ala Thr Gly Gly Lys Pro Gly
    210                 215                 220
```

```
Met Thr Asp Arg Ile Leu His Gly Pro Asp Ser Gln Gln Ala Phe Ser
225                 230                 235                 240

Gln Trp Ala Glu Ser Leu Leu Asp Tyr Ala Thr Leu Met Asp Phe Ser
            245                 250                 255

Thr Glu Ser Leu Gln Pro Ile Trp Ala Leu Ala Asp Lys Pro Glu Arg
        260                 265                 270

Arg Val Glu Leu Glu Asp Ala Phe Pro Glu Phe Met Lys Gln Ser Gln
    275                 280                 285

Gln Ser Ile Pro Lys Val Asp Lys Val Leu Leu Met Asp Ala Arg Pro
290                 295                 300

Pro Met Val Lys Ala Gly Glu Asp Ser Gly Ser Gly Ala Ser Glu Asp
305                 310                 315                 320

Leu Ala Val Phe Asn Pro Ser Thr Ser Asn Gly Tyr Lys Met Val Gly
                325                 330                 335

Gln Phe Gly Gln Arg Asn His Ala Ser Val Ala Asp Gly His Ala Pro
            340                 345                 350

Ile Phe Lys Asp Leu Phe Asp Leu Gly Val Leu Lys Ala Pro Val Gly
        355                 360                 365

Trp Gln Arg Val Trp Asp Asp Ala Gly Ser Gly Lys Ser Lys Asp Tyr
    370                 375                 380

Ala Cys Trp Arg Ala Ile Pro Pro Gln Gly Tyr Arg Ala Leu Gly Asp
385                 390                 395                 400

Val Met Met Leu Ala Thr Ser Gly Tyr Asn Pro Asn Leu Pro Asp
                405                 410                 415

Tyr Val Cys Val His Gln Ser Leu Cys Ala Asp Val Gln Thr Leu Gln
                420                 425                 430

Asn Arg Val Trp Trp Asp Lys Gly Thr Gly Ala Arg Lys Asp Val Ser
            435                 440                 445

Leu Trp Gln Pro Gly Ala Ala Gly Ala Val Ala Ser Ser Cys Phe Ala
450                 455                 460

Gly Val Pro Asn Tyr Asn Asn Pro Pro Asn Ser Gly Asp Ile Glu Arg
465                 470                 475                 480

Leu Arg Gly Ser Ile Ala Cys Val Lys Thr Ser Ala Ile Ala Ser Met
                485                 490                 495

Gln Glu Met Lys Ser Met Leu Ser Gln His Gln Gly Met Glu Ala Met
            500                 505                 510

Met Ser Lys Leu
        515

<210> SEQ ID NO 5
<211> LENGTH: 536
<212> TYPE: PRT
<213> ORGANISM: Artificial sequence
<220> FEATURE:
<223> OTHER INFORMATION: AXMI-205(evo24)

<400> SEQUENCE: 5

Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60
```

```
Val His Thr Tyr Phe His Ser Asp Phe Lys Gln Asp Val Ser Lys Glu
 65                  70                  75                  80

Ile Glu Glu Tyr Arg Glu Lys Met Ser Gln His Val Gly Val Ser Gly
                 85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
            115                 120                 125

Val Leu Trp Tyr Ile Ser Leu Pro Gly Ala Ala Thr Leu Arg Ser Met
130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
            370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
            405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Asp Lys Gly Thr Gly Ala Arg
            450                 455                 460

Lys Asp Val Ser Leu Trp Gln Pro Gly Ala Ala Gly Ala Val Ala Ser
465                 470                 475                 480
```

```
Ser Cys Phe Ala Gly Val Pro Asn Tyr Asn Asn Pro Asn Ser Gly
            485                 490                 495

Asp Ile Ala Arg Leu Arg Gly Ser Ile Ala Cys Val Lys Thr Ser Ala
500                 505                 510

Ile Ala Ser Met Gln Glu Met Lys Ser Met Leu Ser Gln His Gln Gly
            515                 520                 525

Met Glu Ala Met Met Ser Lys Leu
530                 535

<210> SEQ ID NO 6
<211> LENGTH: 536
<212> TYPE: PRT
<213> ORGANISM: Artificial sequence
<220> FEATURE:
<223> OTHER INFORMATION: AXMI-205(evo25)

<400> SEQUENCE: 6

Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
                20                  25                  30

Glu Ser Leu Leu Gly Gln Pro Leu Phe Asp Phe Gly Gly Glu Leu Asp
            35                  40                  45

Ser Ile Glu Ile Glu Gly Arg Ser Tyr Thr Phe Pro Arg Ser Met His
50                  55                  60

Val His Thr Tyr Phe His Ser Asp Phe Lys Gln Asp Val Ser Lys Glu
65                  70                  75                  80

Ile Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
                100                 105                 110

Asp Gln Gln Leu Thr Glu Ile Thr Tyr Ser Ser Thr Arg Glu Ala His
            115                 120                 125

Val Leu Trp Tyr Ile Ser Leu Pro Gly Ala Ala Thr Leu Arg Ser Met
130                 135                 140

Leu Arg Arg Asp Phe Arg Asp Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Ala Glu Met Ser Tyr Lys Ala
                195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
290                 295                 300
```

```
Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
        435                 440                 445

Gln Thr Leu Gln Asn Arg Val Trp Trp Asp Lys Gly Thr Gly Ala Arg
    450                 455                 460

Lys Asp Ala Ser Leu Trp Gln Pro Gly Ala Ala Gly Val Ala Ser
465                 470                 475                 480

Ser Cys Phe Ala Gly Val Pro Asn Tyr Asn Asn Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His Gln Gly
        515                 520                 525

Met Glu Ala Met Met Ser Lys Leu
    530                 535

<210> SEQ ID NO 7
<211> LENGTH: 526
<212> TYPE: PRT
<213> ORGANISM: Artificial sequence
<220> FEATURE:
<223> OTHER INFORMATION: AXMI-205(trun10)

<400> SEQUENCE: 7

Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Tyr Ser Ser Thr Arg Glu Ala His
        115                 120                 125
```

Val Leu Trp Tyr Ile Ser Leu Pro Gly Ala Ala Thr Leu Arg Ser Met
            130                 135                 140

Leu Arg Arg Asp Phe Arg Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
            195                 200                 205

Leu Val Gly Glu Ile Lys Ile Glu His Gly Ser Glu Met Glu Lys Gln
210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
            275                 280                 285

Lys Pro Glu Arg Arg Val Glu Leu Glu Asp Ala Phe Pro Glu Phe Met
290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
            355                 360                 365

Gly His Ala Pro Ile Phe Lys Asp Leu Phe Asp Leu Gly Val Leu Lys
        370                 375                 380

Ala Pro Val Gly Trp Gln Arg Val Trp Asp Asp Ala Gly Ser Gly Lys
385                 390                 395                 400

Ser Lys Asp Tyr Ala Cys Trp Arg Ala Ile Pro Pro Gln Gly Tyr Arg
                405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Pro Pro Asn Ser Gly
                485                 490                 495

Asp Ile Glu Arg Leu Arg Gly Ser Ile Ala Cys Val Lys Thr Ser Ala
            500                 505                 510

Ile Ala Ser Met Gln Glu Met Lys Ser Met Leu Ser Gln His
        515                 520                 525

<210> SEQ ID NO 8
<211> LENGTH: 516
<212> TYPE: PRT

<213> ORGANISM: Artificial sequence
<220> FEATURE:
<223> OTHER INFORMATION: AXMI-205(trun20)

<400> SEQUENCE: 8

Met Ala Ser Ala Ala Asn Ala Gly Gln Leu Gly Asn Leu Pro Gly Val
1               5                   10                  15

Thr Ser Met Gly Met Gly Tyr Asp Val Asn Gly Leu Tyr Ala Ser Pro
            20                  25                  30

Glu Ser Leu Leu Gly Gln Pro Leu Phe Asp Phe Gly Glu Leu Asp
        35                  40                  45

Ser Ile Glu Ile Glu Gly Arg Ser Tyr Thr Phe Pro Arg Ser Met His
    50                  55                  60

Val His Thr Tyr Phe His Ser Asp Phe Lys Gln Asp Val Ser Lys Glu
65                  70                  75                  80

Ile Glu Glu Tyr Arg Glu Lys Met Ser Gln His Val Gly Val Ser Gly
                85                  90                  95

Arg Tyr Lys Leu Phe Ser Ala Ser Leu Ser Val Asp Phe Thr Thr Thr
            100                 105                 110

Asp Gln Gln Leu Thr Glu Ile Thr Tyr Ser Ser Thr Arg Glu Ala His
        115                 120                 125

Val Leu Trp Tyr Ile Ser Leu Pro Gly Ala Ala Thr Leu Arg Ser Met
130                 135                 140

Leu Arg Arg Asp Phe Arg Asp Leu Asn Asn Pro Asn Met Pro Ala
145                 150                 155                 160

Met Glu Leu Phe Lys Arg Tyr Gly Pro Tyr Tyr Ile Ser Glu Ala Ala
                165                 170                 175

Val Gly Gly Arg Leu Asp Tyr Ser Ala Ala Ser Lys Thr Leu Lys Met
            180                 185                 190

Asp Ser Ser Gln Ser Leu Ser Thr Thr Ala Glu Met Ser Tyr Lys Ala
        195                 200                 205

Leu Val Gly Glu Ile Lys Ile Glu His Gly Ser Glu Met Glu Lys Gln
    210                 215                 220

Val Asn Ser Phe Arg Ser Asn Ser Thr Ile Arg Leu Thr Ala Thr Gly
225                 230                 235                 240

Gly Lys Pro Gly Met Thr Asp Arg Ile Leu His Gly Pro Asp Ser Gln
                245                 250                 255

Gln Ala Phe Ser Gln Trp Ala Glu Ser Leu Leu Asp Tyr Ala Thr Leu
            260                 265                 270

Met Asp Phe Ser Thr Glu Ser Leu Gln Pro Ile Trp Ala Leu Ala Asp
        275                 280                 285

Lys Pro Glu Arg Arg Val Glu Leu Glu Asp Ala Phe Pro Glu Phe Met
    290                 295                 300

Lys Gln Ser Gln Gln Ser Ile Pro Lys Val Asp Lys Val Leu Leu Met
305                 310                 315                 320

Asp Ala Arg Pro Pro Met Val Lys Ala Gly Glu Asp Ser Gly Ser Gly
                325                 330                 335

Ala Ser Glu Asp Leu Ala Val Phe Asn Pro Ser Thr Ser Asn Gly Tyr
            340                 345                 350

Lys Met Val Gly Gln Phe Gly Gln Arg Asn His Ala Ser Val Ala Asp
        355                 360                 365

Gly His Ala Pro Ile Phe Lys Asp Leu Phe Asp Leu Gly Val Leu Lys
    370                 375                 380

Ala Pro Val Gly Trp Gln Arg Val Trp Asp Asp Ala Gly Ser Gly Lys

| | | | | | | | | | | | | | | |
|---|---|---|---|---|---|---|---|---|---|---|---|---|---|---|
| 385 | | | | | 390 | | | | | 395 | | | | 400 |

Ser Lys Asp Tyr Ala Cys Trp Arg Ala Ile Pro Pro Gln Gly Tyr Arg
            405                 410                 415

Ala Leu Gly Asp Val Met Met Leu Ala Thr Ser Gly Tyr Asn Pro Pro
            420                 425                 430

Asn Leu Pro Asp Tyr Val Cys Val His Gln Ser Leu Cys Ala Asp Val
            435                 440                 445

Gln Thr Leu Gln Asn Arg Val Trp Trp Asp Lys Gly Thr Gly Ala Arg
            450                 455                 460

Lys Asp Val Ser Leu Trp Gln Pro Gly Ala Ala Gly Ala Val Ala Ser
465                 470                 475                 480

Ser Cys Phe Ala Gly Val Pro Asn Tyr Asn Asn Pro Pro Asn Ser Gly
            485                 490                 495

Asp Ile Glu Arg Leu Arg Gly Ser Ile Ala Cys Val Lys Thr Ser Ala
            500                 505                 510

Ile Ala Ser Met
        515

<210> SEQ ID NO 9
<211> LENGTH: 1608
<212> TYPE: DNA
<213> ORGANISM: Artificial sequence
<220> FEATURE:
<223> OTHER INFORMATION: synthetic sequence encoding AXMI-205

<400> SEQUENCE: 9

| | |
|---|---|
| atggcctccg ccgccaatgc tggccagctg ggcaacctcc ccggcgtcac ctccatgggc | 60 |
| atgggatatg atgtcaatgg cctctatgct tctccagaga gcttgctggg gcagccgctc | 120 |
| tttgattttg gaggagagct ggacagcatc gagatagaag aagaagcta caccttccca | 180 |
| agaagcatgc atgttcacac ctacttccat tcagatttca gcaagatgt cagcaaggag | 240 |
| atcgaggagt acagggagaa gatgagccag catgttggag tttctggaag atacaagctc | 300 |
| ttctccgcct ccctctccgt ggacttcacc accactgatc agcagctgac agagatcacc | 360 |
| tacagctcaa caagagaagc tcatgttctc tggtacatct ccctccccgg cgcggccacc | 420 |
| tgaggagca tgctgcgccg cgacttcaga gatgatctca acaaccccaa catgccggcc | 480 |
| atggagctct tcaagagata tggcccctac tacatctcag aagctgctgt tgaggaagg | 540 |
| ctggactaca gcgccgccag caagaccttg aagatggaca gcagccaaag cctctccacc | 600 |
| accgccgaga tgagctacaa ggcgctggtg ggagagatca agattgagca tggatcagag | 660 |
| atggagaagc aggtgaacag cttcagaagc aacagcacca tcaggctcac cgccactgga | 720 |
| ggaaagccag gatgacaga caggattctt catggacctg cagccagca ggccttctcc | 780 |
| caatgggcgg agagcttgct ggattatgcc accttgatgg acttctcaac agaaagcctc | 840 |
| cagcccatct gggcgctcgc cgacaagcca gaaagaaggg tggagctgga ggatgccttc | 900 |
| cctgagttca tgaagcaaag tcagcagagc atccccaagg tggacaaggt gctgctgatg | 960 |
| gatgcaaggc cgccgatggt gaaggctgga gaagattctg gatctggagc ttcagaagat | 1020 |
| cttgctgtgt tcaacccctc caccagcaat ggctacaaga tggtgggcca gtttggccaa | 1080 |
| aggaaccatg cttctgttgc tgatggccat gctcccatct tcaaggacct cttcgaccte | 1140 |
| ggcgtgctga aggctcctgt tggatggcag cgcgtctggg atgatgctgg atcagggaag | 1200 |
| agcaaggatt atgcttgctg gagggccatc cctcctcaag ctacagagc tcttggagat | 1260 |
| gtcatgatgc tggccaccte aggctacaac cctccaaatc ttccagatta tgttgtgtt | 1320 |

| catcaaagcc tctgtgctga tgttcaaacc ctccagaaca gggtttggtg ggacaaagga | 1380 |
| actggagcaa ggaaggatgt cagcttgtgg cagcctggag ctgctggagc tgtagcaagc | 1440 |
| agctgctttg ctggagttcc aaactacaac aaccctccaa actcaggaga cattgagagg | 1500 |
| ctgagaggaa gcattgcctg cgtcaagacc tccgccattg cttccatgca agagatgaag | 1560 |
| agcatgctct cccagcatca agggatggag gccatgatga gcaagctg | 1608 |

<210> SEQ ID NO 10
<211> LENGTH: 1608
<212> TYPE: DNA
<213> ORGANISM: Artificial sequence
<220> FEATURE:
<223> OTHER INFORMATION: synthetic sequence encoding AXMI-205

<400> SEQUENCE: 10

| atggcctctg ctgccaacgc tggacaactc ggcaacctac aggtgtgac ttccatgggc | 60 |
| atgggatacg acgtaaatgg cctttatgct tctcctgaga gcttgctggg gcagccgctc | 120 |
| tttgattttg gaggagagct ggacagcatc gagatagaag gaagaagcta caccttccca | 180 |
| agaagcatgc atgttcacac ctacttccat tcagatttca gcaagatgt cagcaaggag | 240 |
| atcgaggagt acagggagaa gatgagccag catgttggag tttctggaag atacaagctc | 300 |
| ttctccgcct ccctctccgt ggacttcacc accactgatc agcagctgac agagatcacc | 360 |
| tacagctcaa caagagaagc tcatgttctc tggtacatct ccctccccgg cgcggccacc | 420 |
| ttgaggagca tgctgcgccg cgacttcaga gatgatctca caacccccaa catgccggcc | 480 |
| atggagctct tcaagagata tggcccctac tacatctcag aagctgctgt tggaggaagg | 540 |
| ctggactaca cgccgccag caagaccttg aagatggaca gcagccaaag cctctccacc | 600 |
| accgccgaga tgagctacaa ggcgctggtg ggagagatca agattgagca tggatcagag | 660 |
| atggagaagc aggtgaacag cttcagaagc aacagcacca tcaggctcac cgccactgga | 720 |
| ggaaagccag ggatgacaga caggattctt catggacctg acagccagca ggccttctcc | 780 |
| caatgggcgg agagcttgct ggattatgcc accttgatgg acttctcaac agaaagcctc | 840 |
| cagcccatct gggcgctcgc cgacaagcca gaaagaaggg tggagctgga ggatgccttc | 900 |
| cctgagttca tgaagcaaag tcagcagagc atccccaagg tggacaaggt gctgctgatg | 960 |
| gatgcaaggc cgccgatggt gaaggctgga gaagattctg gatctggagc ttcagaagat | 1020 |
| cttgctgtgt tcaaccctc caccagcaat ggctacaaga tggtgggcca gtttggccaa | 1080 |
| aggaaccatg cttctgttgc tgatggccat gctcccatct tcaaggacct cttcgacctc | 1140 |
| ggcgtgctga aggctcctgt tggatggcag cgcgtctggg atgatgctgg atcagggaag | 1200 |
| agcaaggatt atgcttgctg gagggccatc cctcctcaag ctacagagc tcttggagat | 1260 |
| gtcatgatgc tggccaccct caggctacaa cctccaaatc ttccagatta tgtttgtgtt | 1320 |
| catcaaagcc tctgtgctga tgttcaaacc ctccagaaca gggtttggtg ggacaaagga | 1380 |
| actggagcaa ggaaggatgt cagcttgtgg cagcctggag ctgctggagc tgtagcaagc | 1440 |
| agctgctttg ctggagttcc aaactacaac aaccctccaa actcaggaga cattgagagg | 1500 |
| ctgagaggaa gcattgcctg cgtcaagacc tccgccattg cttccatgca agagatgaag | 1560 |
| agcatgctct cccagcatca agggatggag gccatgatga gcaagctg | 1608 |

<210> SEQ ID NO 11
<211> LENGTH: 1608
<212> TYPE: DNA

<213> ORGANISM: Artificial sequence
<220> FEATURE:
<223> OTHER INFORMATION: synthetic sequence encoding AXMI-205

<400> SEQUENCE: 11

```
atggcgagtg ctgccaacgc cgggcagctg ggaaacctgc ccggcgtgac cagcatgggg      60
atgggatatg atgtgaacgg gctctatgcg agcccggaga gcttgctggg gcagccgctc     120
tttgattttg gaggagagct ggacagcatc gagatagaag gaagaagcta caccttccca     180
agaagcatgc atgttcacac ctacttccat tcagatttca gcaagatgt cagcaaggag      240
atcgaggagt acagggagaa gatgagccag catgttggag tttctggaag atacaagctc     300
ttctccgcct ccctctccgt ggacttcacc accactgatc agcagctgac agagatcacc     360
tacagctcaa aagagaagc tcatgttctc tggtacatct ccctccccgg cgcggccacc      420
tgaggagca tgctgcgccg cgacttcaga gatgatctca caaccccaa catgccggcc       480
atggagctct tcaagagata tggcccctac tacatctcag aagctgctgt tggaggaagg     540
ctggactaca gcgccgccag caagacctttg aagatggaca gcagccaaag cctctccacc    600
accgccgaga tgagctacaa ggcgctggtg ggagagatca agattgagca tggatcagag     660
atggagaagc aggtgaacag cttcagaagc aacagcacca tcaggctcac cgccactgga    720
ggaaagccag ggatgacaga caggattctt catggacctg acagccagca ggccttctcc    780
caatgggcgg agagcttgct ggattatgcc accttgatgg acttctcaac agaaagcctc    840
cagcccatct gggcgctcgc cgacaagcca gaaagaaggg tggagctgga ggatgccttc    900
cctgagttca tgaagcaaag tcagcagagc atccccaagg tggacaaggt gctgctgatg    960
gatgcaaggc cgccgatggt gaaggctgga gaagattctg gatctggagc ttcagaagat   1020
cttgctgtgt caaccctctc accagcaat ggctacaaga tggtgggcca gtttggccaa    1080
aggaaccatg cttctgttgc tgatggccat gctcccatct tcaaggacct cttcgacctc   1140
ggcgtgctga aggctcctgt tggatggcag cgcgtctggg atgatgctgg atcagggaag   1200
agcaaggatt atgcttgctg gagggccatc cctcctcaag gctacagagc tcttggagat   1260
gtcatgatgc tggccacctc aggctacaac cctccaaatc ttccagatta tgtttgtgtt   1320
catcaaagcc tctgtgctga tgttcaaacc ctccagaaca gggtttggtg ggacaaagga   1380
actggagcaa ggaaggatgt cagcttgtgg cagcctggag ctgctggagc tgtagcaagc   1440
agctgctttg ctggagttcc aaactacaac aaccctccaa actcaggaga cattgagagg   1500
ctgagaggaa gcattgcctg cgtcaagacc tccgccattg cttccatgca agagatgaag   1560
agcatgctct cccagcatca agggatggag gccatgatga gcaagctg               1608
```

<210> SEQ ID NO 12
<211> LENGTH: 6403
<212> TYPE: DNA
<213> ORGANISM: Chromobacterium sp.
<220> FEATURE:
<221> NAME/KEY: CDS
<222> LOCATION: (1352)..(2959)

<400> SEQUENCE: 12

```
caccgcgcgc tgaccgtggg ccgggatctg gacatgggcg ggctggatta cgctctgctg     60
gaagcgaggg ggccgcagca atggccgttg cgtgctggcc agacagaggg ccaggcgagg    120
cgctacgtcg acggcgtctt cgccaccgac gacggcaagg cgcgtttcca cgcgatcgat    180
taccggcctc cggcggacaa gatatcggcc cactatccgt tccgattgat caccggccgt    240
```

```
ctgcgcgatc aatggcacgg catgagccgc accgggcgcg tgcccggcct gttttcccac        300
agtccggagc cggagctgcg catgcatccg aagacgccg agcggaggag tctgcgcgac         360
ggcgatctgg tccgcgtcgc cagcaagcgc gggctgtggg tgttgccgct gaagaccgac        420
ggcgatctga cgcggggttg cgtgttcgcc gccatgcatt ggagtcggca gttcctcagc        480
agcggcggca gcaacgaagc aaccacctcg gcggtcgacg gattgtcgtt ccagccggaa        540
ctcaagcacg cggcggtgaa ggtggaaaag gctgagctgc cctggagggt gctggccgcg        600
ttgcgccatc cggatttgtc ggccttgcag gcggaattga cgccgctgtt ggggaatatg        660
gcctatgcgg cgatctcgct ggcggcggga aatgtcttgc tgttgcgcgc tgccgattcc        720
gctgccaggc cggattggct ggcgcgcttg ctggacgcgc tggcgctgcg cccgggaccg        780
gatgcgctgg agtaccgcga cgacgggcga ggcgtgctca agcgcgtggc ctggaatggc        840
gaccggctgg cgggattggt tttcgccggc ggcgggcagg cggaccgcga cgcgggcgaa        900
agcttgctgc aacggctgct ggatggccag ccatggctgg ggccgcggca tgccgcgttt        960
tctcccggcg ggacgcgcgc cgccaagcgg accgcatcg tgtgtcaatg caagcaggtg        1020
ggcgaggccg ccattttgga caggctgcgg caggggcagg acttggcgga gttgaaggcc        1080
gagttgtggg tgcggcgccgt ctgcggttcc tgcgcgccgg agctggcgcg aatggccgcc       1140
aacactgcgc aaaacgtttg agcgggcatg cgcggctgga tggcgcgttt caaggatcga        1200
gaggcggatg gccgtcgcgc cttgttccag cgcaaacgag ttccgtaatt ttactgatcg        1260
gaggaccagc ggcatggccg tgggatgggc gctatatatc tagcggcgtt gtgaaaatgc        1320
cattcgatta taacgttaag aaaggaattc c atg gca tcc gca gca aat gca           1372
                                   Met Ala Ser Ala Ala Asn Ala
                                    1               5 ggt cag ctt ggc aac ctc ccc ggc gtt act tcc atg ggc atg ggc tat           1420
Gly Gln Leu Gly Asn Leu Pro Gly Val Thr Ser Met Gly Met Gly Tyr
         10                  15                  20 gac gtg aat ggt ttg tac gcc agc ccg gaa agc ctg ctt ggc caa ccc           1468
Asp Val Asn Gly Leu Tyr Ala Ser Pro Glu Ser Leu Leu Gly Gln Pro
     25                  30                  35 ttg ttc gat ttc ggc ggc gag ctg gac agc atc gaa atc gag ggc cgc           1516
Leu Phe Asp Phe Gly Gly Glu Leu Asp Ser Ile Glu Ile Glu Gly Arg
40                  45                  50                  55 agc tac acc ttt ccc cgc agc atg cat gta cac acc tat ttc cat tcc           1564
Ser Tyr Thr Phe Pro Arg Ser Met His Val His Thr Tyr Phe His Ser
                 60                  65                  70 gac ttc aaa cag gat gtc agc aag gaa atc gaa gag tat cgg gag aaa           1612
Asp Phe Lys Gln Asp Val Ser Lys Glu Ile Glu Glu Tyr Arg Glu Lys
             75                  80                  85 atg agc cag cac gtg ggc gtg tcc ggc cgc tac aag ttg ttc agc gct           1660
Met Ser Gln His Val Gly Val Ser Gly Arg Tyr Lys Leu Phe Ser Ala
         90                  95                 100 tcg ctg agc gtg gat ttc acc acc acg gac cag caa ctg acc gag att           1708
Ser Leu Ser Val Asp Phe Thr Thr Thr Asp Gln Gln Leu Thr Glu Ile
     105                 110                 115 acc tac agc tcc acc cgc gaa gcc cat gtg ctg tgg tac atc agc ctg           1756
Thr Tyr Ser Ser Thr Arg Glu Ala His Val Leu Trp Tyr Ile Ser Leu
120                 125                 130                 135 cct ggc gcg gcc acg ctg cgt tcg atg ctg cgc cgc gat ttc cgc gac           1804
Pro Gly Ala Ala Thr Leu Arg Ser Met Leu Arg Arg Asp Phe Arg Asp
                 140                 145                 150 gac ctg aac aac ccc aat atg ccg gcc atg gag ctg ttc aag cgc tat           1852
Asp Leu Asn Asn Pro Asn Met Pro Ala Met Glu Leu Phe Lys Arg Tyr
             155                 160                 165
```

-continued

| | |
|---|---|
| ggt ccc tac tac ata tcg gaa gcg gcg gtg ggc ggc cgg ctg gac tac<br>Gly Pro Tyr Tyr Ile Ser Glu Ala Ala Val Gly Gly Arg Leu Asp Tyr<br>170               175                 180 | 1900 |
| agc gcg gcc agc aag acc ttg aag atg gac agc agc cag tcg ctg tcc<br>Ser Ala Ala Ser Lys Thr Leu Lys Met Asp Ser Ser Gln Ser Leu Ser<br>185               190                195 | 1948 |
| acc acc gcc gaa atg tcc tac aag gcg ctg gtg ggc gag atc aag atc<br>Thr Thr Ala Glu Met Ser Tyr Lys Ala Leu Val Gly Glu Ile Lys Ile<br>200               205            210            215 | 1996 |
| gag cat ggc tcg gag atg gaa aag cag gtc aac agc ttc cgc agc aac<br>Glu His Gly Ser Glu Met Glu Lys Gln Val Asn Ser Phe Arg Ser Asn<br>220               225                230 | 2044 |
| tcc acc atc cgt ctc acc gcc acc ggc ggc aag ccg ggc atg acc gat<br>Ser Thr Ile Arg Leu Thr Ala Thr Gly Gly Lys Pro Gly Met Thr Asp<br>235               240                245 | 2092 |
| cgc ata ctg cac ggt ccg gat tcg cag cag gcg ttc tcg caa tgg gcg<br>Arg Ile Leu His Gly Pro Asp Ser Gln Gln Ala Phe Ser Gln Trp Ala<br>250               255                260 | 2140 |
| gaa tcg ctg ctc gac tat gcg acg ctg atg gac ttt tcc acc gaa agc<br>Glu Ser Leu Leu Asp Tyr Ala Thr Leu Met Asp Phe Ser Thr Glu Ser<br>265               270                275 | 2188 |
| ctg caa ccg atc tgg gcg ctg gcc gac aag ccc gag cgc cgc gtc gag<br>Leu Gln Pro Ile Trp Ala Leu Ala Asp Lys Pro Glu Arg Arg Val Glu<br>280               285            290            295 | 2236 |
| ctt gag gac gcc ttc ccc gaa ttc atg aag cag tcg cag cag tcc atc<br>Leu Glu Asp Ala Phe Pro Glu Phe Met Lys Gln Ser Gln Gln Ser Ile<br>300               305                310 | 2284 |
| ccc aag gtg gac aag gtg ctg ctg atg gac gcg cgg ccg cct atg gtg<br>Pro Lys Val Asp Lys Val Leu Leu Met Asp Ala Arg Pro Pro Met Val<br>315             320                325 | 2332 |
| aag gct ggg gag gat agc ggc tcc ggc gcg tcg gag gat ctg gct gtg<br>Lys Ala Gly Glu Asp Ser Gly Ser Gly Ala Ser Glu Asp Leu Ala Val<br>330               335                340 | 2380 |
| ttc aat ccc agc acc tcc aat ggc tac aag atg gtt ggc cag ttc ggt<br>Phe Asn Pro Ser Thr Ser Asn Gly Tyr Lys Met Val Gly Gln Phe Gly<br>345             350                355 | 2428 |
| cag cgc aac cat gcc agc gtg gcg gat ggc cat gcg ccg att ttc aag<br>Gln Arg Asn His Ala Ser Val Ala Asp Gly His Ala Pro Ile Phe Lys<br>360             365            370            375 | 2476 |
| gat ctg ttc gat ctg ggc gtg ctg aag gcg ccg gtg ggt tgg cag cgg<br>Asp Leu Phe Asp Leu Gly Val Leu Lys Ala Pro Val Gly Trp Gln Arg<br>380             385                390 | 2524 |
| gtg tgg gac gac gcc ggc tcc ggc aag tcc aag gac tac gcg tgc tgg<br>Val Trp Asp Asp Ala Gly Ser Gly Lys Ser Lys Asp Tyr Ala Cys Trp<br>395             400                405 | 2572 |
| cgc gcg att ccg ccg cag ggc tac cgc gcg ctg ggc gat gtg atg atg<br>Arg Ala Ile Pro Pro Gln Gly Tyr Arg Ala Leu Gly Asp Val Met Met<br>410             415            420 | 2620 |
| ctg gcc acc agc ggc tat aac ccg ccg aat ctg ccg gac tat gtt tgc<br>Leu Ala Thr Ser Gly Tyr Asn Pro Pro Asn Leu Pro Asp Tyr Val Cys<br>425             430            435 | 2668 |
| gtg cat caa agc ctg tgc gcg gat gtg cag acg ctg caa aac cgg gtg<br>Val His Gln Ser Leu Cys Ala Asp Val Gln Thr Leu Gln Asn Arg Val<br>440             445            450            455 | 2716 |
| tgg tgg gac aag ggc acc ggc gcg cgc aag gat gtc agc ctg tgg caa<br>Trp Trp Asp Lys Gly Thr Gly Ala Arg Lys Asp Val Ser Leu Trp Gln<br>460             465            470 | 2764 |
| ccg ggc gcg gcc ggc gcg gtg gcg tcc tct tgc ttc gcc ggc gtg cct<br>Pro Gly Ala Ala Gly Ala Val Ala Ser Ser Cys Phe Ala Gly Val Pro | 2812 |

-continued

```
                                475                     480                     485
aat tac aac aac ccg ccc aat tcc ggc gac atc gag cgc ttg cgc ggc             2860
Asn Tyr Asn Asn Pro Pro Asn Ser Gly Asp Ile Glu Arg Leu Arg Gly
                490                     495                     500 agc atc gca tgc gtg aag acc agc gcg atc gcg tcc atg cag gaa atg             2908
Ser Ile Ala Cys Val Lys Thr Ser Ala Ile Ala Ser Met Gln Glu Met
505                     510                     515 aag tcc atg ctc agc cag cac caa ggc atg gaa gcg atg atg tcc aag             2956
Lys Ser Met Leu Ser Gln His Gln Gly Met Glu Ala Met Met Ser Lys
520                     525                     530                     535 ctg tgatccgggc ctgaccgggc aaaaaaacaa ggctgccgga tggcagcctt                  3009
Leu gttttatccc accgtctgcg ccaggcggga cgggttcagt tgaagcggta gtccaccgtc           3069
acgccgaccg tgcgcggcgc gcctatcacc cccagattgt tgccgcgggc cggaatctgg           3129
gcgtagagca cgccttggtt ggtcagattg ttgacgtagg cgcgtacccc ccagcgggcg           3189
tcctcgtagc cggtgttcag gttggccacg atgtagtcgc cggcggtgcg ggccggatca           3249
ttggtgatgt ccgaatagta ggacccgacg cggttcaggc tgccgccaat atagaagttg           3309
cgcggcagac gctgcttgaa gcccaggttg actgtcagat gcggcgcgta gttgaactga           3369
ttgccttgta tgccgggatt ggcggcgtcg gtgccggtca ccttggtgtt caacaggccg           3429
atgccggcgc tgagggtcag cttcggcgtg acgcgcgctt tgctttccag ttccaggccg           3489
tagctttgcc cttccggaat attggtgaag cgcgacccca gtatggcctg gtagccggtg           3549
tactggttga agaaggcatt ggcgttgagg ctgacgcgct cgtccaggaa ggtggagcgg           3609
ctgctcagct cgtaggttgt gacctgttcc ttgttgaagg tgtagtactt gttgtcgttg           3669
tccaggccgg agccgccggc gttgtagcct ttgcgcgcgg acaggcccag ggtggtggat           3729
gggctgtact tgtagctcag gccggccttg gcaggaaca aggtttcgcc gaggtcatag            3789
ctggcttgag cttcgtagct ctgtccgggg cccagcgtgg tgttgcgtcg ttgcatctcg           3849
cgttccgcgc ggccgcccag attgaggctc cacttgtcgt ctagcgccag cgtggcttcg           3909
ccgtaaaacg cctcggtctt gaggcgatcc ttggccgcta cgcgcggaga ggcgttcatg           3969
tcctggtcgc ggtcgtagta atagacgccg accaagccgc tcagccagcc atcctgcggc           4029
gcgtaggcca ggcgggcctc ggcggtgttg cccttctcgt ccagcctcat gctgaatgcg           4089
ggcgtgtcgg aatctttgaa cgcgctgatg ttgtcgcgct ggcccagcag caggctggcg           4149
ctccaggcgt cattgatctg gtatcgcaga tcggcgctga cggtgttgtt gaacgagtcc           4209
tgatagcgag cttcggtcga caggcggtga tactggtagt cgaagtagtt gccgtcgacg           4269
tagttcaggt attcgcccttt gttcttgcgg tgcgccaccg tcagcttggc ggtgaagccc         4329
ggcagcgcgc tgggcttcca cagcagcttg ccgcggaagc tgctgttttt cacttcggac          4389
gcgtcccagg gcatggcgcc cggataatcg atgtagctgt ggccgttcag gccttcggcg          4449
gcgacgcgaa aagccagctc gtcggtgatc ggaccggaga tcatgccggc cagcgtcact          4509
ttgccgtcct tattctcata gccggcgcgc agcgcgcctt cccagtcgaa agtcgggtcc          4569
ttggtgttga ccacgatggc gccggccatg gtattgcggc cctgagtggt ggactgcggg          4629
ccgcgcagca cttctatctg ttccacgtcc catgggctgg cgtcgacgta gcgctggccg          4689
ttccagcttt ccgacatgcc gtcaaccgtg gtgctgacgc gcgggcggga gccggagacc          4749
agcgtgttgt agccggtgcc ggggccggtg ccttccacgc cgcggatatt gatgatgccg          4809
gcgccgttgg ccgtggcgtt gggggtggcg gccgccgcgt catagaccga tttgatctcg          4869
```

```
ccggtgtcgg tgtcgcgcag caccgatacc gcggtggtgg tgtctttcag cgagcggttg    4929
atcttctcgc cggtgacggt cacggtaggc agggcggcgt cttgttggtc ggccggagcc    4989
gccagcgcgg agtggggcag cgacatgcct cccaggcagg ccaaggccag cagggtggcg    5049
tgggccaggg cgtcgcgctt gcggtgcggg agttttttcca tcgttccaga ttcctcattg    5109
tggttattgt cagattgacc ggggcggtt ctgcggcgtc gtctggctgg cgaggaatcg    5169
ttggctaatg cggcggacgg aactgtgggg ccggtgctga cccgttgaga tcgttgcgat    5229
caacagatgc aaatgataat atttatcatt aacaatatgc ataacttaa cgcgaatcga    5289
attggccggt agcggccgca ttcattcgcg ggcctggatc ggtggagaac gttgtggaat    5349
ggaatcaagt ggcagtggaa agcgcggctt ggctgcaaca cccggaagcg ggcaaaccgc    5409
aatggtggga ccggctggcc gccgcgggcg cgccgctgcg agagcggctg ccggacgggc    5469
gcgtatgcgt gactttcctg tggcgggatc cggccggtgg tcccgccgct tcgtccatcg    5529
tccgtgtgta cgccgacgtc aactccgtca ccgatcacca tagcccgcag ccgcaatcgt    5589
tgtcccgcct gggcgatacc gacgtctggt ggtggcaggc ggtgttgccg gcggattggc    5649
gcggtagtta cgcctatatc ccggtagcgg ccggacagac gcctcccgtt cccggcggcg    5709
atgtccgcca gagccggctt cttcatcgcg aatggtggct gagcatcatg gcccaggccg    5769
tcgccgatcc gctcaacccc gccgccgact accgcagcag ctggggcgcc agcttgtcgc    5829
cgctgcatct gcccgacgcc ccggaccagt ccgcctgggc cgcctgggac aaaaccgggc    5889
agggggccga tccgcgccgc ctgacggaaa tccgctggga cagcgccatg ctcggcaagg    5949
cgcgccgggt ctggatctac cacacggggcg agatttctgt cggacaatgg gccgagaggc    6009
cgctggcgat tttgctggac ggccagcatt gggcgcagcg cctgccggtg ttcgccgcgc    6069
tggacgagga cacccgccgc ggccgtttgc cgcccgcggt gtatttgctg atcgacagca    6129
tcgacggcaa gcaccgcgag gaagacttgc cctgcaacgc cgcattctgg gctggccttg    6189
caaaggaact gctgccgcag gcggctctga tcgcgccgtt cagcggccgg ccgattgca    6249
ccgtggtggc cgggcagagc tatggcggcc tggctgccga tgttcgccgg cctcaactgg    6309
ccggaccgtt tcggctgcgt gctcagccag tccggctcgt tctggtggcc acacgtggaa    6369
ttgcatgaaa aggcgcgcgc ggcaagcgcc cgcc                                  6403
```

<210> SEQ ID NO 13
<211> LENGTH: 4
<212> TYPE: PRT
<213> ORGANISM: Artificial sequence
<220> FEATURE:
<223> OTHER INFORMATION: endoplasmic reticulum targeting peptide

<400> SEQUENCE: 13

Lys Asp Glu Leu
1

<210> SEQ ID NO 14
<211> LENGTH: 510
<212> TYPE: PRT
<213> ORGANISM: Photorhabdus luminescens

<400> SEQUENCE: 14

Met Ser Asn Asp Lys Thr Gly Lys Ser Leu Glu Gln Glu Asn Ser Glu
1               5                   10                  15

Arg Asp Val Glu Ile Arg Asp Arg Asn Tyr Phe Arg Lys Leu Ser Leu
            20                  25                  30

-continued

```
Phe Asp Asp Thr Val Ile Ala Gly Ala Glu Met Ile Gly Thr Ser Tyr
        35                  40                  45
Asp Val Phe Gly Lys Tyr Cys Asn Val Gly Ser Cys Met Asn Ser Leu
 50                  55                  60
Phe Asp Glu Arg Lys Ile Asn Ala Ser Glu Asp Asn Phe Lys Lys Val
 65                  70                  75                  80
Thr Ile Leu Gly Lys Thr Leu Lys Val Pro Tyr Tyr Ile Asp Cys Tyr
                 85                  90                  95
Ser Val Gly Asp Leu Lys Tyr Thr Asn Ala Ser Gly Glu Ser Ile Glu
             100                 105                 110
Ser Tyr Gln Ser Asn Ile Ser Ser Lys Ser Arg Ile Lys Gly Asn Tyr
             115                 120                 125
Leu Phe Phe Ser Ala Ser Leu Lys Val Asp Phe Asp Thr Asp Ser Leu
130                 135                 140
Thr Asp Phe Glu Asn Ala Phe Ser Arg Ile Gln Tyr Thr Tyr Asp Leu
145                 150                 155                 160
Tyr Ile Leu Lys Ser Ser Ala Glu Ala Leu Lys Glu Phe Leu Lys Glu
                165                 170                 175
Ser Val Lys Thr Ala Leu Asp Lys Ala Asp Thr Glu Glu Asp Met Asn
            180                 185                 190
Asp Leu Phe Asn Thr Trp Gly Ser His Phe Leu Ser Gly Val Val Met
            195                 200                 205
Gly Gly Cys Ala Gln Tyr Ser Ser Thr Asn Lys Tyr Thr Ser Asn
210                 215                 220
Leu Thr Asn Ser Phe Asp Val Ala Ala Ser Phe Ala Gly Phe
225                 230                 235                 240
Ile Gly Leu Ser Ala Arg Thr Gly Asn Ser Phe Met Glu Asp Ile Lys
                245                 250                 255
Lys Phe Arg Ser Ala Ser Asn Ile Lys Thr His Ala Ile Gly Gly Asp
            260                 265                 270
Leu Ser Arg Phe Asp Pro Phe Gly Gly Ala Thr Ser Ala Asp Gln Pro
            275                 280                 285
Ser Ala Glu Glu Ile Ala Ala Ala Lys Lys Ala Phe Glu Asp Trp Lys
290                 295                 300
Ala Ser Val Pro Asn Ala Pro Glu Leu Val Asn Phe Ala Asp Ser Asn
305                 310                 315                 320
Pro Leu Thr Gly Ile Trp Glu Leu Cys Ser Asp Arg Thr Gln Lys Ala
                325                 330                 335
Lys Leu Lys Lys His Phe Glu Thr Val Trp Ala Pro Ala Glu Ser Ala
            340                 345                 350
Lys Arg Arg Val His Ala Asp Tyr Ile Asp Glu Ile Ile Gly Ile
            355                 360                 365
Asn Asn Thr Asn Thr Pro Pro Glu Gly Tyr Ile Gly Leu Lys Ser Thr
370                 375                 380
Lys Asp Glu Asn Leu Asn Ser Lys Gly Asn Ile Cys Leu Phe Met His
385                 390                 395                 400
Lys Ala Lys Tyr Asp Pro Asn Ile Asp Asn Lys Asp Cys Ile Thr Glu
                405                 410                 415
Leu Lys Phe Ile Thr Val Arg Asp Lys Ser Pro Glu Gly Asp Trp Val
            420                 425                 430
Lys Ile Pro Gln Asp Ile Tyr Ile Ser Pro Asn Gln Tyr Leu Tyr Leu
            435                 440                 445
Cys Tyr Leu Pro Ala Lys Tyr Ser Ala Glu Lys Ala Ile Lys Asp Ile
```

```
                    450               455                  460
Gln Leu Leu Cys Ser Ser Cys Gly Ser Ser Met Ile Leu Pro Tyr Gly
465                 470                  475                 480

Tyr Asn Asp Val Leu Asp Glu Arg Gly Glu Arg Ala Asn Ala Thr Glu
                    485                  490                 495

Asp Asp Asn Val His Tyr Leu Ile Tyr Ser Ala Gly Trp Lys
                500                  505                 510

<210> SEQ ID NO 15
<211> LENGTH: 470
<212> TYPE: PRT
<213> ORGANISM: Clavibacter michiganensis

<400> SEQUENCE: 15

Met Ser Asp Phe Phe Val Thr Glu Thr Asp Thr Pro Arg Ile Leu Pro
1               5                   10                  15

Gly Val Ser Leu Thr Gly Ser Thr Tyr Asp Val Phe Gly Asp Asp Ala
                20                  25                  30

Thr Asn Asp Ser Ala Ile Phe Gln Ile Phe Asp Trp Ser Lys Ala Glu
            35                  40                  45

Trp Gly Thr Thr Glu Ile Asn Gly Thr Glu Tyr Arg Ile Pro Lys Leu
        50                  55                  60

Met Asn Ala Glu Gly Val Ala Gly Ser Glu Tyr Val Ser Ile Tyr Gly
65                  70                  75                  80

Asn Thr Val Glu Glu Tyr Gln Gln Ser Leu Ala Ala Ser Val Ala Val
                85                  90                  95

Ser Gly Ser Asn Met Phe Phe Ser Gly Ser Leu Glu Thr Gln Phe Gly
                100                 105                 110

Ser Ser Ser Met Arg Arg Ser Glu Asn Ala Phe Ser Arg Val Glu Gln
            115                 120                 125

Val Val Lys Leu Trp Ser Ile Gly Leu Pro Pro Ser Lys Lys Leu Arg
130                 135                 140

Glu Leu Leu Ser Gly Ser Phe Leu Glu Ala Leu Asp Gly Leu Pro Ala
145                 150                 155                 160

Ala Ala Ser Thr Ser Glu Glu Gln Ala Glu Tyr Lys Gly Phe Leu Asp
                165                 170                 175

Thr Trp Gly Ala Phe Tyr Leu Ser Gly Met Leu Ile Gly Gly Lys Thr
            180                 185                 190

Leu Phe Thr Ser Ser Val Asn Lys Leu Thr Val Asp Arg Thr Leu Ser
        195                 200                 205

Ile Ser Val Thr Ala Asp Leu Ser Tyr Lys Ser Val Thr Gly Gln Ile
210                 215                 220

Ser Asn Glu Asp Lys Ile Lys Tyr Ala Ser Gln Leu Ser Gln Phe Ala
225                 230                 235                 240

Ser Ser Ser Asn Thr Val Lys Asn Ala Phe Gly Gly Asn Pro Ala Leu
                245                 250                 255

Ala Ser Arg Val Phe Asp Gly Arg Val Gln Tyr Asp Glu Trp Ser Ala
            260                 265                 270

Ser Val Ala Gln Asn Pro Val Ile Val Arg Phe Asp Gly Thr Arg Pro
        275                 280                 285

Leu Thr Gly Val Trp Thr Leu Cys Ser Thr Pro Glu Arg Gly Lys Ile
    290                 295                 300

Leu Glu Ser Tyr Phe Asp Asp Lys Trp Ala Pro Ala Arg Ser Leu Glu
305                 310                 315                 320
```

```
Leu Ser His Phe Pro Asp Val Val Asp Asp Leu Thr Val Val Val Gly
            325             330                 335
Asn Asp Asp Gln Pro Pro Val Pro Asp Gly Tyr Thr Lys Asp Asp Tyr
            340             345                 350
Asp Leu Asn Arg His Ala Gly Gly Lys Phe Ile Tyr Leu Cys Trp His
            355             360             365
Lys Val Pro Val Ser Gly Leu Arg Lys Pro Lys Arg Val Leu Gln Ala
            370             375             380
Met Gln Val Ile Tyr Asn Gly Asp Lys Val Pro Asp Gly Tyr Ser Lys
385                 390             395                     400
Ile Asn Val Asp Leu Asn Gln Gly Ala Gly Gly Asp Asp Val Phe Leu
                405             410                 415
Cys Met Lys Gln Gly Glu Tyr Gly Thr Asp Glu Asn Ile Leu Asp Val
            420             425             430
Arg Val Ile Gly Gly Asn Asp Ser Phe Val Pro Ala Pro Tyr Gly Tyr
        435             440             445
Lys Thr Leu Pro Gly Asp Leu Asn Lys Gly Ala Gly Gly Asp Tyr Val
    450             455             460
Tyr Ile Ala Tyr Ala Asn
465             470
```